United States Patent
Smith et al.

(10) Patent No.: US 6,855,366 B2
(45) Date of Patent: Feb. 15, 2005

(54) NITRIC OXIDE-MODIFIED LINEAR POLY (ETHYLENIMINE) FIBERS AND USES THEREFOR

(75) Inventors: Daniel J. Smith, Stow, OH (US); Darrell H. Reneker, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 10/738,582

(22) Filed: Dec. 16, 2003

(65) Prior Publication Data

US 2004/0131753 A1 Jul. 8, 2004

Related U.S. Application Data

(62) Division of application No. 09/571,444, filed on May 16, 2000, now Pat. No. 6,737,447.
(60) Provisional application No. 60/158,673, filed on Oct. 8, 1999.

(51) Int. Cl.$^7$ .............................. B05D 1/00; A61L 15/04; A61F 2/00
(52) U.S. Cl. ...................... 427/2.1; 427/2.24; 427/2.31; 623/926; 424/426; 977/DIG. 1
(58) Field of Search ................................. 427/2.1, 2.24, 427/2.31; 623/926; 424/426

(56) References Cited

U.S. PATENT DOCUMENTS

| | | |
|---|---|---|
| 4,043,331 A | 8/1977 | Martin et al. ................ 128/156 |
| 4,524,036 A | 6/1985 | Gilding et al. ................ 264/10 |
| 5,024,789 A | 6/1991 | Berry |
| 5,376,117 A | 12/1994 | Pinchuk et al. |
| 5,519,020 A | 5/1996 | Smith et al. ................ 424/718 |
| 5,714,511 A | 2/1998 | Saavedra et al. ........... 514/426 |
| 5,770,645 A | 6/1998 | Stamler et al. ............. 524/419 |
| 5,814,656 A | 9/1998 | Saavedra et al. ........... 514/426 |
| 6,106,913 A | 8/2000 | Scardino et al. |
| 6,645,518 B2 * | 11/2003 | Tedeschi et al. ............ 424/423 |

FOREIGN PATENT DOCUMENTS

| | | | |
|---|---|---|---|
| EP | 0 030 786 | * | 6/1981 |
| WO | WO 96 32136 A | | 10/1996 |
| WO | WO 98 03267 A | | 1/1998 |

OTHER PUBLICATIONS

Pulfer, Sharon K. et al.: "Incorporation of Nitric Oxide–Releasing Crosslinked Polyethyleneimine Microsperes into Vascular Grafts," *Journal of Biomedical Materials Research*, vol. 37, no. 2, 1997, pp. 182–189.

Doshi, J. et al.: "Electrospinning Process and Applications of Electrospun Fibers," *Journal of Electrostatics*, Aug. 1995, Netherlands, vol. 35, no. 2–3, pp. 151–160.

Smith, Daniel J. et al.: "Nitric Oxide–Releasing Polymers Containing the (N(O)NO)—Group," *Journal of Medicinal Chemistry*, vol. 39, no. 5, 1996, pp. 1148–1156.

Bauer, Joseph A. et al.: "Evaluation of Linear Polyethyleneimine/Nitric Oxide Adduct on Wound Repair: Therapy versus Toxicity," *Wound Repair and Regeneration*, vol. 6, no. 6, Nov., 1998, pp. 569–577.

* cited by examiner

*Primary Examiner*—Tae H. Yoon
(74) *Attorney, Agent, or Firm*—Roetzel & Andress LLP

(57) ABSTRACT

A novel coating for medical devices provides nitric oxide delivery using nanofibers of linear poly(ethylenimine) diazeniumdiolate. Linear poly(ethylenimine) diazeniumdiolate releases nitric oxide (NO) in a controlled manner to tissues and organs to aid the healing process and to prevent injury to tissues at risk of injury. Electrospun nano-fibers of linear poly(ethylenimine) diazeniumdiolate deliver therapeutic levels of NO to the tissues surrounding a medical device while minimizing the alteration of the properties of the device. A nanofiber coating, because of the small size and large surface area per unit mass of the nanofibers, provides a much larger surface area per unit mass while minimizing changes in other properties of the device.

10 Claims, No Drawings

NITRIC OXIDE-MODIFIED LINEAR POLY (ETHYLENIMINE) FIBERS AND USES THEREFOR

This application claims benefit of pending U.S. Provisional Application No. 60/158,673 filed on Oct. 8, 1999 and is a Divisional of Ser. No. 09/571,444 filed May 16, 2000, now U.S. Pat. No. 6,737,447.

TECHNICAL FIELD

This invention relates to the production of fibers of linear poly(ethylenimine) modified with nitric oxide (NO). More particularly, the present invention relates to the use of these NO-modified linear poly(ethylenimine) fibers that can be applied to medical devices such as catheters, stents, vascular grafts, wound dressings, and the like, to release therapeutic levels of NO for wound healing or other medical purposes. Specifically, the present invention relates to the production of electrospun nanofibers of linear poly(ethylenimine) diazeniumdiolate for use in the delivery of NO to a patient.

BACKGROUND OF THE INVENTION

The importance of nitric oxide (NO) in biological repair mechanisms is well known even though the precise mechanism of its action has not been completely elucidated. NO is known to inhibit the aggregation of platelets and to reduce smooth muscle proliferation, which is known to reduce restenosis. When delivered directly to a particular site, it has been shown to prevent or reduce inflammation at the site where medical personnel have introduced foreign objects or devices into the patient.

Researchers have sought various ways to deliver NO to damaged tissue and to tissues and organs at risk of injury. NO can be delivered systemically, but such delivery can bring undesired side effects with it. Ideally, NO should be delivered in a controlled manner specifically to those tissues and organs that have been injured or are at risk of injury. Various compounds have been used to deliver NO therapeutically. Diazeniumdiolates (NONOates) exhibit the ability to release NO spontaneously. Other classes of NO donors either require activation to release therapeutic levels of nitric oxide, or they release both NO and undesired free radicals.

The use of NONOates for the release of nitric oxide to specifically treat tissue that has been injured or is at risk of injury during sepsis or shock has been described in at least Saavedra et al. U.S. Pat. No. 5,814,656, the disclosure of which is incorporated herein by reference. Insoluble polymeric NONOates have also been generally described in Smith et al. U.S. Pat. No. 5,519,020, the disclosure of which is also incorporated herein by reference. These polymers were used to deliver NO to specific tissues, and results have shown that controlled release of NO to a specific site greatly reduced the inflammation and accelerates the healing process at that site. However, heretofore, these compositions have had to be delivered either by topical application or by coating onto the medical device. While such applications have been successful, the need continues to exist to provide a manner in which the NONOate compositions could be exposed to a greater surface area of the medical devices to which they are applied. The use of NONOates as coatings on implantable medical devices is also disclosed in Stamler et al. U.S. Pat. No. 5,770,645, the disclosure of which is also incorporated herein by reference.

In addition to the need set forth hereinabove, the process of coating some medical devices, particularly implantable devices, may have adverse effects on and alter the physical properties of the device. This can contribute to serious complications from the body's own defense to the medical device as foreign material.

The technique of electrostatic spinning, also known within the fiber forming industry as electrospinning, of liquids and/or solutions capable of forming fibers, is well known and has been described in a number of patents as well as in the general literature. The process of electrostatic spinning generally involves the introduction of a liquid into an electric field, so that the liquid is caused to produce fibers. These fibers are generally drawn to a cathode for collection. During the drawing of the liquid, the fibers harden and/or dry. This may be caused by cooling of the liquid, i.e., where the liquid is normally a solid at room temperature; by evaporation of a solvent, e.g., by dehydration (physically induced hardening); or by a curing mechanism (chemically induced hardening).

Fibers produced by this process have been used in a wide variety of applications, and are known, from U.S. Pat. Nos. 4,043,331 and 4,878,908, the disclosures of which are incorporated herein by reference, to be particularly useful in forming non-woven mats suitable for use in wound dressings and prosthetic devices. One of the major advantages of using electrostatically spun fibers is that these fibers can be produced having very thin diameters, usually on the order of about 100 nanometers to about 25 microns, and more preferably, on the order of about 100 nanometers to about 1 micron. Thus, these fibers can be collected and formed into coatings or non-woven membranes of any desired shape and thickness. It will be appreciated that, because of the very small diameter of the fibers, the resultant coating or membrane will have very small interstices and high surface area per unit mass.

Linear poly(ethylenimine) (L-PEI) is known to be a water insoluble polymer, but soluble in alcohols and other organic solvents. In order to electrospin fibers, the polymer must first be in liquid form (i.e., soluble). However, in order to be useful as a NO-releasing complex, the polymer must be capable of being converted to a diazeniumdiolate (NONOate) and should be insoluble in all solvents once formed.

Thus, the need exists for a method for coating or otherwise depositing diazeniumdiolate-modified fibers, and particularly, linear poly(ethylenimine) fibers, onto medical devices in a manner which suitably provides for the release of therapeutic amounts of NO to a particular site.

SUMMARY OF INVENTION

It is, therefore, an object of the present invention to provide a medical device comprising at least one nanofiber of a polymeric nitric oxide donor that forms a coating layer on the device.

It is another object of the present invention to provide a medical device comprising at least one nanofiber of a polymeric diazeniumdiolate derivative that forms a coating layer on the device.

It is yet another object of the present invention to provide a medical device comprising at least one nanofiber of linear poly(ethylenimine) diazeniumdiolate derivative that forms a coating layer on the device.

It is still another object of the present invention to provide a medical device comprising at least one nanofiber, wherein the nanofibers provide a greater surface area to unit mass ratio than ordinary topical coatings.

It is still another object of the present invention to provide at least one nanofiber, as above, which is capable of being coated or otherwise applied to medical devices.

It is a further object of the present invention to provide a medical device, as above, wherein the device is coated with at least one electrostatically spun nanofiber of a polymeric nitric oxide donor.

It is still another object of the present invention to provide an improved medical device, as above, wherein the device is coated with nanofibers of crosslinked linear poly (ethylenimine) diazeniumdiolate.

It is yet another object of the present invention to provide an improved medical device, as above, wherein the electrostatically spun nanofibers are directly spun onto the medical device.

It is still another object of the present invention to provide a method of making a medical device comprising at least one nanofiber of linear poly(ethylenimine) forming a coating layer on the device.

In general, the present invention provides a method for the production of at least one fibers of linear poly(ethylenimine) diazeniumdiolate using electrospinning techniques. Such fibers have very small diameters of less than 1 micron, and, more preferably, less than 400 nanometers. The fibers also have very high surface areas per unit mass and are capable of releasing therapeutic levels of NO as needed.

Other aspects of the present invention are achieved by a coating for a medical device comprising at least one electrospun fibers of linear poly(ethylenimine) diazeniumdiolate. A coating containing these fibers has a much larger surface area per unit mass than do topical coatings previously employed, and have minimal effect to the properties of the medical devices employed. The fiber-coated medical devices are capable of releasing therapeutic levels of nitric oxide to a particular site of a patient.

The present invention further provides a medical device having at least one electrospun fibers comprising a polymeric NONOate deposited thereon. Such medical devices may include catheters, stents, vascular grafts, wound dressings, and other related medical devices which may be implanted or otherwise invade a patient's body.

EMBODIMENTS FOR CARRYING OUT THE INVENTION

As noted hereinabove, the present invention is directed toward the production of very small diameter fibers (on the order of nanometers) of linear poly(ethylenimine) modified with nitric oxide (NO). These fibers, when deposited on medical devices as a coating or the like, may release therapeutic levels of NO at the site where the medical device has been implanted or otherwise rests in the patient. The term medical device is intended to encompass all types of medical devices, including those used in connection with either external or internal treatment of a mammal. Medical devices used in the external treatment of a mammal include, but are not limited to, wound dressings, burn dressings or other skin coverings, and surgical thread. Medical devices used in the internal treatment of a mammal include, but are not limited to, vascular grafts, stents, catheters, valves, artificial joints, artificial organs, and surgical thread.

In order to produce the fibers of the present invention, linear poly(ethylenimine) must first be obtained. Linear poly(ethylenimine) may be prepared by any method known in the art or may be obtained commercially, if available. One well known and published method of synthesizing linear poly(ethylenimine) is by hydrolysis of poly(2-ethyl-2-oxazoline). This method is well known to those skilled in the art and, therefore, details of the process are not provided herein. Typically, the poly(2-ethyl-2-oxazoline) should have a number average molecular weight of about 500,000, although smaller or larger molecular weights should not readily affect the formation of linear poly(ethylenimine). In a preferred embodiment, the linear poly(ethylenimine) synthesized should have a molecular weight ranging from about 100,000 to about 500,000, although higher or lower molecular weights are not seen as materially affecting the essential nature of the invention, provided of course, the compound can be effectively dissolved in the desired solvent for use in electrospinning fibers therefrom. Preferably, linear poly (ethylenimine) having a molecular weight of about 200,000 is employed.

Linear poly(ethylenimine) is known to be water insoluble, but soluble in alcohols or other organic solvents. In one embodiment of the present invention, the polymer is exposed to nitric oxide in chloroform/acetonitrile or in methanol/sodium methoxide as set forth in Scheme I hereinbelow. Upon exposure, the polymer is converted to a diazeniumdiolate derivative of linear poly(ethylenimine).

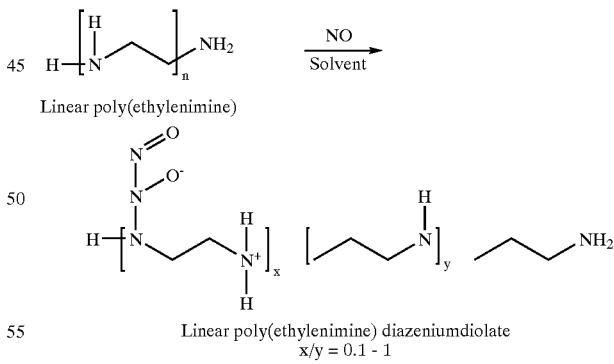

Importantly, once modified, it has been found that the polymer remains soluble in low molecular weight alcohols such as ethanol or methanol. The diazeniumdiolate-modified polymer can therefore be dissolved in the alcohol to provide an alcohol solution suitable for electrospinning into fibers. The concentration of the alcohol solution is not believed to be materially important to the success of the invention, provided of course that the solution is capable of dissolving the linear poly(ethylenimine) derivative. Typically, about 10 percent by weight of linear poly(ethylenimine) may be dissolved in the solution, although higher or lower amounts can be used without departing from the scope or spirit of the invention. Upon the formation of the fibers, they can be either directly or indirectly deposited onto the medical devices as needed for use as coatings thereon. These fibers typically have a diameter in the range of from about 100 nanometers to about 5 microns, more preferably, in the range of from about 100 nanometers to about 1 micron, and most preferably in the range of about 100 nanometers to about 400 nanometers. In light of the diameter size of the fibers, these fibers are often termed "nanofibers."

It will be appreciated that the resultant nanofibers have very high surface areas per unit mass. Thus, when these fibers are used to form a the coatings, the resultant coatings will have very small intertices and high surface areas per unit mass.

In an alternative embodiment shown in Scheme II hereinbelow, linear poly(ethylenimine) is dissolved in a preferably low molecular weight alcoholic solvent, and the resultant solution is electrospun into fibers which are then deposited onto a medical device in a manner similar to that set forth above. It is at this point that the polymeric fiber-coated device is treated with or otherwise exposed to nitric oxide to convert the fibers from linear poly(ethylenimine) nanofibers to those modified with NO, namely by converting the polymer into a diazeniumdiolate derivative of the linear poly(ethylenimine).

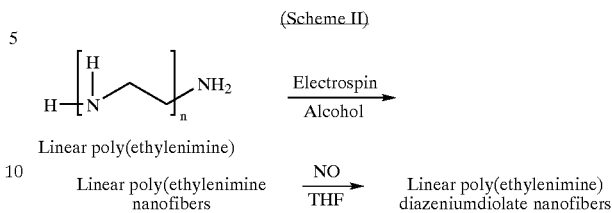

It will be appreciated, however, that the resultant fibers are still soluble in various organic solvents. Thus, to render them insoluble in all solvents the polymer must be crosslinked. This can be done by either of two methods. First, as shown in Scheme III, the fibers are spun onto the device, and then treated with a crosslinking agent such as 1,4-butanediol diglycidyl ether (i.e., bis-epoxide) dissolved in small amounts of tetrahydrofuran (THF). More particularly, the fibers are soaked in a small amount of bis-epoxide in THF (from about 1 to about 25 percent by weight per weight of the polymer). The resultant treated linear poly(ethylenimine) diazeniumdiolate nanofibers were then noted to be totally crosslinked and rendered insoluble in all solvents including alcohol and water.

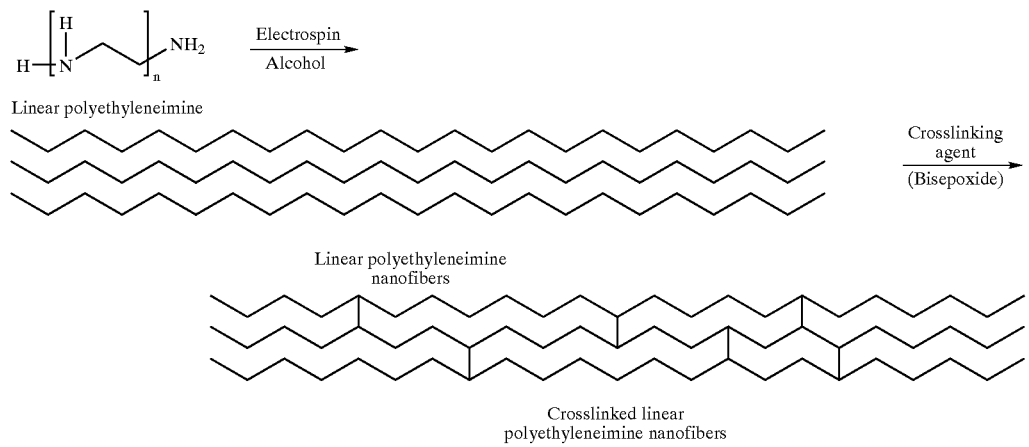

In the second approach, shown in Scheme IV, linear poly(ethylenimine), whether treated with NO or not, is treated with from about 1 to about 25 percent by weight 1,4-butanediol diglycidyl ether (i.e., bis-epoxide) in ethanol and then subsequently electrospun into the desired fibers. Where this process is employed, the crosslinking agent, i.e., the bis-epoxide, becomes resident within the fiber and, upon curing of the fibers at about 80° C. for about 30 minutes or at room temperature for a longer period of time, the fiber become crosslinked and are insoluble in all solvents. If not already so modified (and they preferably are not), the fibers can then be modified with NO to form crosslinked poly (ethylenimine) diazeniumdiolate.

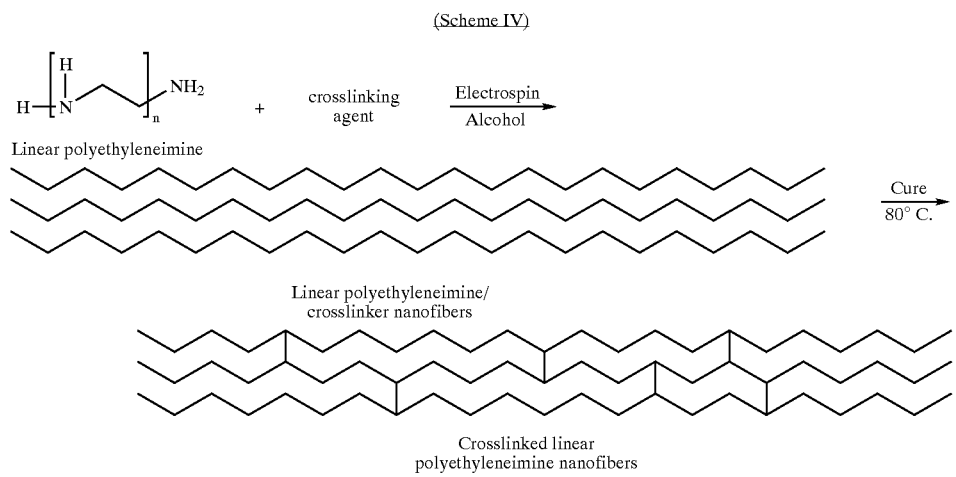

These polymer fibers release NO with a half-life in the range of 6–30 hours at pH 7.4 and 37° C. Once released, NO will help prevent platelet aggregation, smooth muscle cell proliferation and other biological processes.

Thus, it should be evident that the present invention is highly effective in delivering NO to tissues surrounding medical devices while minimizing the alteration of the properties of the devices. This is accomplished by using electrostatically spun nanofibers of polymeric NONOate to coat the medical device. A nanofiber coating, because of the small size and large surface area per unit mass of the nanofibers, provides a much larger surface area while minimizing changes in other properties. Such a coating can be utilized on any implant devices, which would be otherwise likely to cause an inflammatory response, to minimize that response.

Based upon the foregoing disclosure, it should now be apparent that the use of the nanofibers of poly(ethylenimine) diazeniumdiolate as coatings on medical devices will carry out the objects set forth hereinabove. It is, therefore, to be understood that any variations evident fall within the scope of the claimed invention and thus, the selection of specific component elements can be determined without departing from the spirit of the invention herein disclosed and described.

We claim:

1. A method of making a medical device, comprising the steps of:
   (a) providing a solution of linear poly(ethylenimine) in an organic solvent and an untreated medical device;
   (b) subjecting the linear poly(ethylenimine) solution to an electric field such that at least one nanofiber is produced;
   (c) depositing the at least one nanofiber onto a medical device, such that a nanofiber coated medical device is produced.

2. The method of claim 1, comprising the additional step of exposing the linear poly(ethylenimine) to nitric oxide such that a linear poly(ethylenimine) diazeniunidiolate is produced, wherein said additional step takes place prior to the step of subjecting the linear poly(ethylenimine) to an electric field.

3. The method of claim 2, additionally comprising the step of crosslinking the at least one nanofiber of linear poly (ethylenimine) diazeniumdiolate of the nanofiber coated medical device.

4. The method of claim 3, wherein the step of crosslinking comprises treating the at least one nanofiber of linear poly(ethylenimine) diazeniumdiolate with 1,4 butanediol diglycidyl ether in tetrahydofuran solvent and curing the at least one nanofiber by heating to about 80° C. for at least about 30 minutes.

5. The method of claim 1, additionally comprising the step of crosslinking the at least one nanofiber of linear poly (ethylenimine) of the nanofiber coated medical device.

6. The method of claim 5, additionally comprising the step of treating the crosslinked at least one nanofiber of linear poly(ethylenimine) with nitric oxide to create at least one crosslinked nanofiber of linear poly(ethylenimine) diazeniunidiolate.

7. The method of claim 1, wherein the linear poly (ethylenimine) solution subjected to an electric field additional comprises a crosslinking agent, and further comprising the step of curing the resulting at least one nanofiber of the nanofiber coated medical device, such that the at least one nanofiber is crosslinked.

8. The method of claim 7, further comprising the step of treating the at least one crosslinked linear poly (ethylenimine) nanofiber with nitric oxide such that at least one linear poly(ethylenimine) diazeniumdiolate nanofiber is produced.

9. The method of claim 1, additionally comprising the step of treating the at least one linear poly(ethylenimine) and nanofiber of the nanofiber coated medical device with nitric oxide such that at least one linear poly(ethylenimine) diazeniunidiolate nanofiber is produced.

10. The method of claim 9, additionally comprising the step of crosslinking the at least one linear poly (ethylenimine) diazeniumdiolate nanofiber.

* * * * *

UNITED STATES PATENT AND TRADEMARK OFFICE
CERTIFICATE OF CORRECTION

PATENT NO. : 6,855,366 B2
DATED : February 15, 2005
INVENTOR(S) : Smith et al.

It is certified that error appears in the above-identified patent and that said Letters Patent is hereby corrected as shown below:

Column 8,
Lines 6, 46-47 and 61-62, "diazeniunidiolate" should read -- diazeniumdiolate --
Line 37, "tetrahydofuran" should read -- tetrahydrofuran --

Signed and Sealed this

Twenty-fourth Day of May, 2005

JON W. DUDAS
*Director of the United States Patent and Trademark Office*